United States Patent [19]
Burns

[11] Patent Number: 5,757,001
[45] Date of Patent: May 26, 1998

[54] DETECTION OF COUNTERFEIT CURRENCY

[75] Inventor: Donald A. Burns, Los Alamos, N. Mex.

[73] Assignee: The Regents of the University of Calif., Oakland, Calif.

[21] Appl. No.: 641,657

[22] Filed: May 1, 1996

[51] Int. Cl.[6] .................................................. G01N 21/55
[52] U.S. Cl. ........................... 250/339.11; 250/339.09; 250/341.8
[58] Field of Search .................... 250/339.11, 339.09, 250/341.8

[56] References Cited

U.S. PATENT DOCUMENTS 3,867,041  2/1975  Brown et al. ......................... 356/209
5,483,069  1/1996  Kofune et al. ....................... 250/341.8

FOREIGN PATENT DOCUMENTS 52-60200  5/1977  Japan ................................. 250/339.11

OTHER PUBLICATIONS

Technology Detects Fake Money, Stones, Newspaper Journal Journal North, May 12, 1995.
"Tool Could Nab Counterfeiters," *The FLC News Link*, Jun., 1995.
"Spectroscopy Foils Money Counterfeiters," *Photonics Spectra*, Jun. 1995, p. 29.
"Laboratory Technology Could Curtail Counterfeiters," *Newsbulletin*, May 5, 1995, pp. 1+.
"Counterfeit Currency Is No Match for Los Alamos Technology," *Dateline Los Alamos*, Oct. 1995, pp. 1+.
"Finding the Fake," *Modern Maturity*, Sep.–Oct., 1995.
"The Supernote," *The New Yorker*, Oct. 23, 1995, pp. 50–55.
"Fake $100 Bills Worry U.S. Officials," *The Cincinnati Enquirer*, Oct. 16, 1995, p. A1.
"Principal Component Analysis of Diffuse Near–Infrared Reflectance Data from Paper Currency," *Applied Spectroscopy* 43,8 (1989) pp. 1399–1405.

*Primary Examiner*—Constantine Hannaher
*Attorney, Agent, or Firm*—Gemma Morrison Bennett

[57] ABSTRACT

A method of detecting counterfeit currency by contacting the currency to be tested with near infrared beams in the spectrum below 1250 nanometers, measuring reflectance of the near infrared beams and comparing the reflectance values with those from genuine currency.

2 Claims, 18 Drawing Sheets

DETECTION OF COUNTERFEIT CURRENCY

This invention was made with government support under Contract No. W-7405-ENG-36 awarded by the U.S. Department of Energy. The government has certain rights in the invention.

TECHNICAL FIELD

This invention relates to using near-infrared spectroscopy for detecting counterfeit currency.

BACKGROUND ART

Several ways of detecting counterfeit currency have been used with varying degrees of success depending upon the method and depending upon the sophistication of the counterfeiters and quality of the counterfeit bills. Methods used range from simple human visual observation and subjective evaluation to complicated technical methods.

Feel or appearance of bills can sometimes be used to detect counterfeits. A genuine new bill with limited circulation has ink which is raised slightly from the paper as a result of the intaglio printing process used to make authentic United States currency. The raised ink can be felt by lightly running a fingernail across the surface of the bill. Usage of the bill wears the raised ink down. Genuine bills have red and blue silk embedded fibers, some which are strewn about the surface of the bill; these can be dislodged with the point of a pin.

Often counterfeit bills have filled-in or fuzzy squares in the background area around the portrait; genuine bills have background areas around the portraits made up of clear squares with sharp corners. The outermost line framing the portrait on bills which come from the Bureau of Engraving and Printing that were made in 1990 and later is made of extremely fine type that says "THE UNITED STATES OF AMERICA." This can be read only with a magnifying glass, and could possibly be replicated by expert counterfeiters.

Bills issued in 1990 or later have a thin vertical strip of polyester fiber embedded about an inch from the left edge. The strip is printed with the denomination of genuine $10, $20, $50 and $100 bills. The $20 bill, for example, has a vertical strip which says "USA TWENTY," that can be seen when the bill is held up to the light.

Simple methods such as marking bills with felt-tip markers filled with weak iodine solution have been used. The penmark will turn dark brown or black when it reacts with chemicals in cheaper paper used in some counterfeit currency while marks on genuine currency of bills made with similar paper remain yellow.

United States currency has ferrous oxide in the black ink on the front portrait side of bills. The nation's twelve Federal Reserve banks use currency scanners which read the magnetic field down the center line of the portrait on a bill with such precision that a thousand genuine hundred-dollar bills are rejected for every one that is later found to be counterfeit. This, of course, is less efficient than a method which could reject only the bills which are counterfeit.

Other magnetic/conductor devices have been used to detect magnetic ink on genuine bills. The magnetic/conductor device is a hand-sized plastic box that indicates by a beep, light flash, or other signal that the bill is genuine. Unfortunately, dry toner inks in almost all copy machines are also magnetic and conductive, so even a machine-copied image of paper currency will easily pass this detector.

Near infrared spectroscopy using wavelengths from about 2904 $cm^{-1}$ (3443 nanometers) to about 7670 $cm^{-1}$ (1303 nanometers) has been used for quality control in paper manufacturing for grading white bond papers using principal component analysis of multivariate pattern data sets by performing an eigenanalysis to obtain eigenvalues and eigenvectors. Matrix equations are used to obtain elements of the eigenvectors (loadings) which are then squared to determine the relative amounts of information that the corresponding variables contribute to the eigenvector. The data is further manipulated to two dimensional representations, normalized, mean-centered and scaled to unit variances for analysis of samples. It has been suggested that this sort of paper analysis could be used for detection of papers used for counterfeit currency. However, there is still a need for a method of detecting counterfeit currency which is made with authentic or close to authentic papers and for a method which would not be limited to a complicated analysis of only areas on paper currency which have not been inked.

Counterfeiting of United States currency continues to be a problem which is said to be increasing along with the development of better and better printing and reprographic technology and the increasing sophistication and size of industrial scale printing operations. There are said to be billions of dollars of $100 "Supernotes" being printed in the Middle East which are such remarkably good counterfeits that the bills can pass through the Federal Reserve banks undetected.

The Secret Service has been urging the Bureau of Engraving and Printing to make a full-scale redesign of United States currency since 1981 with suggestions of holograms, chemical markers and the use of multiple colors. This solution has been considered unacceptable, primarily for political reasons. The United States Treasury has been reluctant to make basic changes in United States currency because of its effort to promote continued stability of United States currency domestically and abroad and to insure continued public confidence in the United States currency. The United States Treasurer has said that the use of additional colors was never seriously considered because green is the color of prosperity and black shows we are sound and solid and in the black. An amendment to an appropriations bill requires that United States currency paper be supplied by an American-owned concern, thus limiting the choices of suppliers and kinds of paper used for currency.

Confidence in United States currency could be lost if there are large numbers of counterfeit US dollars passed in foreign banking centers and no trustworthy method for accurately detecting counterfeit bills. Therefore, there is still a need for more dependable, accurate methods of detection of counterfeit bills.

It is an object of this invention to provide a method of detection of counterfeit bills.

Other objects of this invention are to provide a method of detection of counterfeit bills which is economical, easy to set up, simple to use, can be portable, and which gives consistently accurate results.

It is a further object of this invention to provide a method of detection of counterfeit currency which can detect counterfeit bills made with authentic papers such as those of higher denominations made from bleached genuine one dollar bills.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

DISCLOSURE OF INVENTION

To achieve the foregoing and other objects, and in accordance with the purposes of the present invention, as embodied and broadly described herein, there has been invented a method of detecting counterfeit currency comprising:

(a) contacting at least one selected area of currency known to be genuine with a near-infrared beam having at least one wavelength in the electromagnetic spectrum below 1250 nanometers;

(b) measuring the intensity of the reflected portion of the portion of said near-infrared beam within said at least one wavelength in the electromagnetic spectrum below 1250 nanometers reflected from said at least one selected area of said currency known to be genuine;

(c) contacting currency to be tested with a near-infrared beam having at least one wavelength in the electromagnetic spectrum substantially identical to said at least one wavelength used to contact said at least one selected area of said currency known to be genuine;

(d) measuring the intensity of the reflected portion of the portion of said near-infrared beam within said at least one wavelength in the electromagnetic spectrum below 1250 nanometers reflected from said at least one selected area of said currency to be tested;

(e) comparing said intensity of said reflected portion of said portion of said near-infrared beam reflected from said currency known to be genuine with said intensity of said reflected portion of said portion of said near-infrared beam reflected from said at least one area of said currency to be tested, in order to determine discrepancies between said intensity measured in (b) and said intensity measured in (d).

In a more particular embodiment, there has been invented a method of detecting counterfeit currency comprising:

(a) contacting at least one selected area of currency known to be genuine with a near-infrared beam having at least two wavelengths in the electromagnetic spectrum below 1250 nanometers;

(b) measuring the intensity of the reflected portion of the portion of said near-infrared beam within said at least two wavelengths in the electromagnetic spectrum below 1250 nanometers reflected from said at least one selected area of said currency known to be genuine;

(c) contacting currency known to be counterfeit with a near-infrared beam having at least two wavelengths in the electromagnetic spectrum below 1250 nanometers reflected from said at least one selected area of said currency known to be counterfeit;

(d) measuring the intensity of the reflected portion of the portion of said near-infrared beam within said at least two wavelengths reflected from said at least one selected area of said currency known to be counterfeit;

(e) plotting the results of steps (b) and (d) to obtain two plots;

(f) comparing said two plots obtained from plotting the results of steps (b) and (d);

(g) selecting at least one wavelength at which said two plots of the results of steps (b) and (d) are most divergent;

(h) contacting currency to be tested with a near-infrared beam having at least one wavelength in the electromagnetic spectrum substantially identical to said at least one wavelength at which said two plots are most divergent;

(i) measuring the intensity of the reflected portion of said near-infrared beam within said at least one wavelength at which said two plots are most divergent which is reflected from said currency to be tested;

(j) comparing said intensity of said reflected portion of said portion of said near-infrared beam reflected from said currency to be tested with said plot obtained from step (b) to determine extent of divergence of portion of said near-infrared beam reflected from said currency to be tested from portion of said near-infrared beam reflected from said currency known to be genuine; thereby enabling a determination of whether said currency to be tested is genuine.

BRIEF DESCRIPTION OF THE DRAWINGS

The accompanying drawings, which are incorporated in and form a part of the specification, illustrate some of the embodiments of the present invention and, together with the description, serve to explain the principles of the invention. In the drawings.

BEST MODES FOR CARRYING OUT THE INVENTION

Figure 1:
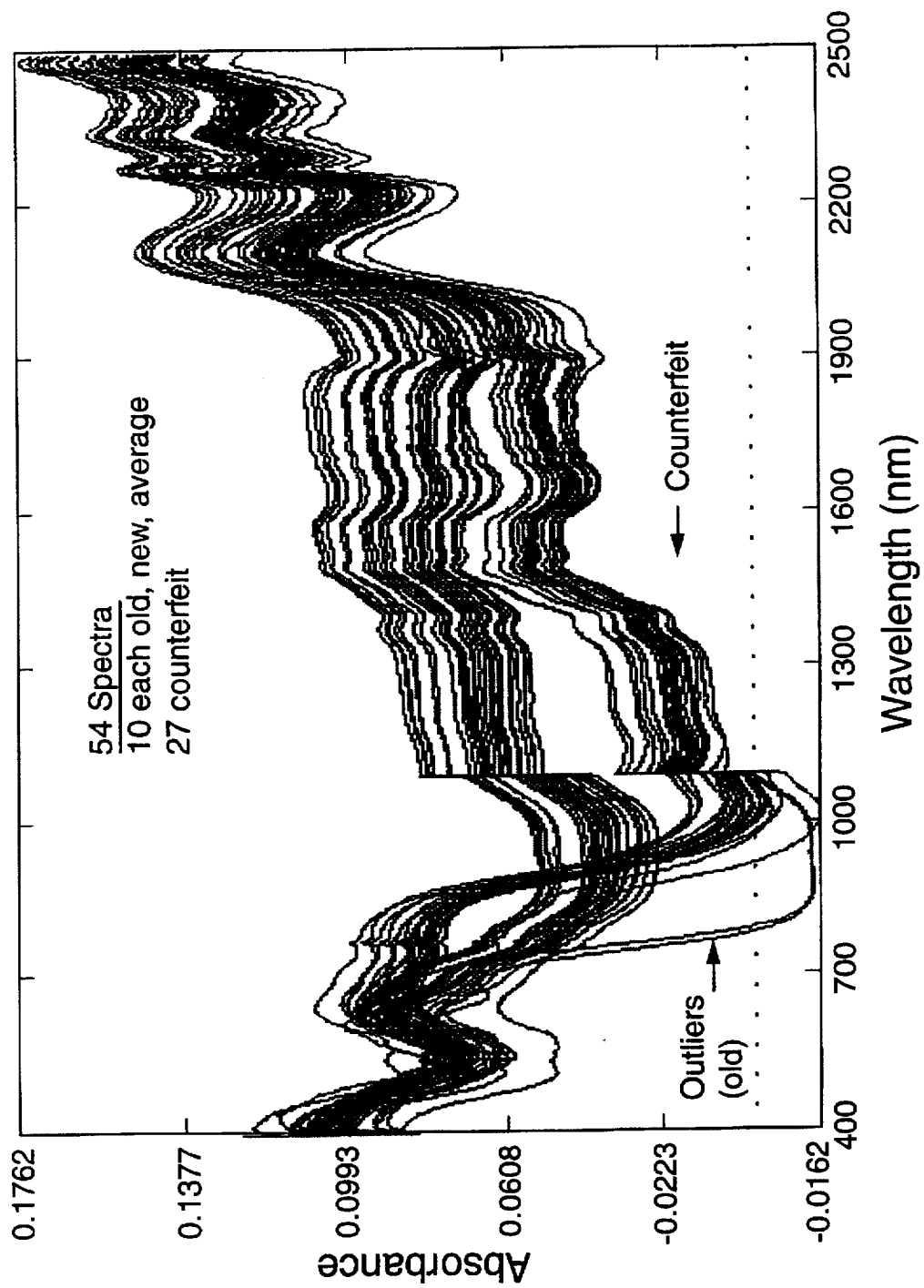
FIG. 1 is a graph of the absorbances at different wavelengths for scans of both genuine and counterfeit currency plotted as a family of tracings.

It has been discovered that reflected portions of near-infrared light beams can be used to detect counterfeit currency using any of several simple methods which can be used by scanning any convenient portion of the currency, whether inked or not. Ways of detecting whether the currency is counterfeit without using any complicated mathematical algorithms such as principal component analysis have been invented.

In each of these methods, samples of currency known to be genuine are contacted with near infrared light just beyond the visible spectrum. The light can be beamed directly onto the currency from a near-infrared beam source or the light from a near-infrared beam source can be transmitted through a fiber optic cable onto the currency.

The currency reflects a portion of the near-infrared beam back to sensors which convert the varying intensities of each of the reflected wavelengths into electrical signals. The sensors are typically semiconductors and can be made from materials such as, for example, lead sulfide, silicon, or indium-gallium-arsenide. Any sensor which will either generate voltage or change its resistance when contacted by reflected near infrared light can be used in the practice of the invention.

The sensor feeds an electrical signal that is a function of the intensity of the reflected light back to the spectrophotometer where it can be stored until required by the accompanying computer. This signal may be either analog or digital; analog signals can be digitized for temporary storage.

White light from a tungsten-halogen lamp, or an equivalent means, is directed through an aperture or slit onto a diffraction grating. The mirror-like grating in the monochromator oscillates through cycles providing wavelengths at a second slit associated with each position of the grating. Light passing through the second slit or aperture is then focused into one end of a fiber optic cable for transmission to a remote reflectance probe.

The reference signals can be obtained ahead of time and retained in a computer memory, or can be obtained on a one time basis either before or after signals from samples to be tested are transmitted to the computer.

After obtaining reflectance/absorbance data from one or more bills that are known to be genuine, reflectance/absorbance data from scans of the same areas on bills that are known to be counterfeit are obtained.

Comparison of plots of the data from these two sets of scans (of genuine currency and of counterfeit currency) are used to determine the particular wavelengths where the largest differences between genuine and counterfeit currency occur. The data from the genuine currency at the selected wavelengths is then stored in the computer as the reference library or reference signals with which the signals from currency being tested can be compared. Alternatively, the data from the genuine currency and from the counterfeit currency used in determining wavelengths at which to scan the currency to be tested can be compared, and the differences in values for genuine and counterfeit currency can be used to choose threshold values above or below which a bill being tested would be identified as being genuine, suspect, or counterfeit.

Once the computer has been trained to distinguish counterfeit from genuine currency, any of several ways to obtain data generated from reflectance at specific wavelengths can be used for operation of the invention. Either an acousto-optic tunable filter module, interference filters, or a monochromator can be used to provide specific wavelengths for use in a dedicated instrument once the desired wavelengths have been determined with a research grade spectrophotometer.

When radio frequency energy from a radio frequency generator is fed to the transducer of an acousto-optic tunable filter module, the frequency of the radio frequency energy sets up a standing wave within a crystal such as, for example, a tellurium oxide crystal in the acousto-optic tunable filter module. The spacing of the standing wave is determined by the radio frequency and the crystal gives the effect of a variable diffraction grating, thereby determining what wavelength will be directed onto the sample.

Fixed interference filters can be used as the selector if it is desired to observe only selected portions of the wavelength spectrum where the largest differences between genuine and counterfeit currency can be observed.

A white light can be passed through an interference filter to obtain a specific wavelength chosen from a large range of wavelengths. One or more fixed interference filters can be tilted to obtain a narrow range of wavelengths when the full spectrum is not needed. Tilting an interference filter away from the normal (perpendicular) direction of the beam being transmitted through it increases the light path within the filter and hence changes the wavelength. Accordingly, tilting such a filter through known angles produces a range of wavelengths, one or more of which can be used as an economical substitute for a scanning monochromator in the practice of this invention after the wavelengths to be used have been selected using a research grade monochromator.

The electrical signals (reflectance data) from the sensor are digitized and fed into a computer for computation of absorbance values. Reflectance values can be converted to absorbance values using the equation:

$$\text{Absorbance} = \text{Log}(1/\text{reflectance})$$

The absorbance data is then plotted as a function of wavelength.

A tracing or plot of the absorbance value as a function of the wavelength from which it came, with reference to any certain area on the bill being tested, produces a "fingerprint" or pattern characteristic of the sample. The paper, inks, and fibers of counterfeit currency are almost certain not to be identical in every respect to the paper, inks, and fibers in the same locations on the bills of genuine currency. Patterns for each type of genuine bill will be similar. Given enough areas, the patterns of genuine bills are clearly different from those produced by testing counterfeit bills.

Adequate discrimination between genuine and counterfeit currency can be obtained using only the absorbances from as few as two wavelengths by using the first derivative of a fall scan of the currency. Bills known to be counterfeit are scanned in the same manner as the genuine bills. Then comparisons of data for different wavelengths reflected from different locations on the surfaces of the bills can be compared to determine at which wavelengths the differences in reflectance between counterfeit and genuine currency of a particular denomination occur. The particular wavelengths where the greatest differences occur can then be used to scan currency for the purpose of determining whether or not the currency is genuine.

The bills to be tested for detection of counterfeiting can be scanned in their entirety by either moving the bills with respect to a near-infrared beam source or by moving a near-infrared beam source with respect to the bills in a stationary position. When the bills are scanned in their entirety, the pattern of absorbance as a function of wavelength can be compared to a pattern of absorbance as a function of wavelength for genuine bills which has been stored in the reference library or data base in the computer memory.

Alternatively, selected portions of the bills to be tested for detection of counterfeiting can be either scanned as the bills are moved with respect to a near-infrared beam source or by moving a near-infrared beam source with respect to the bills in a stationary position. In the case of a moving bill, the near-infrared beam contact with the bill can be timed to hit only the selected portion of the bill.

Another way of scanning less than the entire sample is to obtain spectral data of specific regions through openings in a mask between the spectral probe and the surface of the bill. A mask of any material which has no appreciable near infrared spectrum, such as white Teflon™ (polytetrafluroethylene) or aluminum foil, can be used. Regions having ink, no ink, or a combination of ink and paper can be chosen.

The reflectance data can be treated in a number of ways to get it into a form that will show clear reliably repeatable differences between the data obtained from near-infrared analysis of genuine currency and data obtained from near-infrared analysis of counterfeit currency. Multiple linear regression, partial least squares, principal component regression, and neural networks are examples of data treatments which can be used. Multiple linear regression, often followed by simply taking first or second derivatives, is the presently preferred algorithm for analyzing the reflectance data because other chemometric data treatments, such as principal component analysis, partial least squares or neural networks are much more complex than is required.

When multiple linear regression is employed in the practice of this invention, subsequently taking the first or second derivative of the data can be useful. Although such derivative treatment tends to amplify noise, a major advantage of it is the amplification of the differences between the data representing genuine bills and data representing counterfeit bills. Another advantage is the correction for starting offsets in the spectra and the baseline tilt which makes for a more easily interpreted plot.

There are a number of other ways of manipulating the reflectance data from the selected wavelengths (at which the differences between the genuine and counterfeit currency are largest). For example, the mean spectrum of the absorbance data can be subtracted from each of the spectra before the derivatives are calculated. This treatment tends to emphasize the differences between the groups of genuine currency and counterfeit currency. To further emphasize the differences and to help in identifying the wavelengths where the greatest differences occur, the scales on which the values are plotted can be expanded.

A training set or a database is made using data obtained from scans of genuine currency from different sources, having been manufactured on different dates, and having different conditions and degrees of wear from circulation.

In collecting a library of data for later comparison with bills to be tested, one typically provides a teaching set of 20 to 30 samples each of genuine and counterfeit currency and a confirmation set of a similar number of bills. Old and worn, average condition, and new uncirculated bills which have been printed on varying dates should be used for the training set. However, as few as a half dozen samples of each may be used. Using more than about 30 samples of each is generally not useful because of redundancy of the data obtained.

The algorithms used to construct the training set or database are the same as the algorithms which will be used to manipulate the data obtained from scanning the currency to be tested for determination of whether it is counterfeit or not. The computer does comparison of reflectance data from selected areas on bills scanned to detect counterfeits by comparing that reflectance data with that in the computer library or database of reflectance data from the same selected areas on bills known to be genuine. The comparisons can be of raw reflectance data, or absorbances, or can be pattern recognition comparisons of vectors which have been generated by the computer from the raw reflectance data.

The reflectance data patterns from the bills being tested can be compared with the reflectance data patterns of bills known to be genuine which have been stored in the computer as a database. Alternatively, once the differences between reflectance data patterns for genuine and counterfeit currency have been determined to select the wavelengths where there is greatest divergence in reflectance data, values at certain wavelengths can be selected for use as thresholds above or below which bills being tested would be determined as "suspect" or definitely counterfeit.

The invention can be practiced using any number of wavelengths within a broad range. The more wavelengths used in the generation of the data to be compared when making determinations of whether currency is counterfeit or not, the more accurate the determinations will be. This is true up to the number of wavelengths where use of more wavelengths begins to introduce a noise or unwanted frequency components as the data is forced into too great a multiplicity of equations. Likewise, the more components of the wavelengths evaluated when using principal component algorithms, the more pronounced the data differences between the genuine and counterfeit currency will be.

Using a multiple linear regression algorithm, counterfeit bills can be detected with almost absolute certainty using as few as two wavelengths. Generally, best results can be obtained by use of three or four wavelengths. (Three wavelengths, properly spaced, would approximate a second derivative; four wavelengths would approximate two first derivatives.) With six or more wavelengths, noise or unwanted frequency components begin to reduce the accuracy of the results.

The data obtained from the wavelengths can be plotted in any of several ways, including families of tracings of absorbances as a function of wavelengths, families of tracings of first or second derivatives of values of absorbances as a function of wavelengths, or as two- or three-dimensional clusters.

FIG. 1 is an example of data plotted as a family of tracings of absorbances as a function of wavelengths. It can be noted in FIG. 1 that there is a pattern of greater and lesser divergences between values for genuine currency and for counterfeit currency at differing wavelengths.

Figure 2:
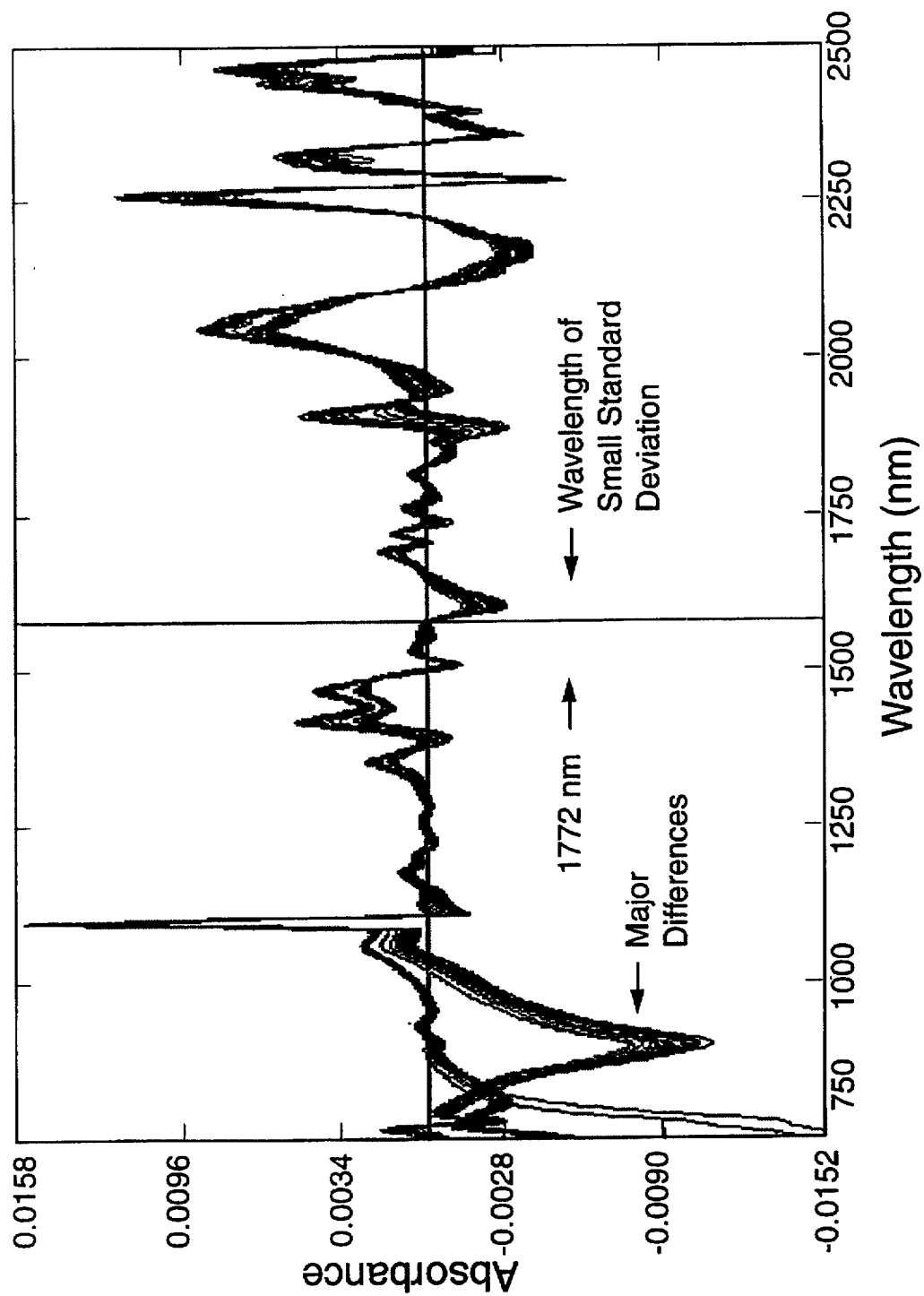
FIG. 2 is a plot of the first derivatives of the same data plotted in FIG. 1.

FIG. 2 shows the first derivatives of the same values as shown in FIG. 1 plotted as a family of tracings. The amplification of the differences between the groups of lines representing genuine currency and lines representing counterfeit currency can readily be seen.

Figure 3:
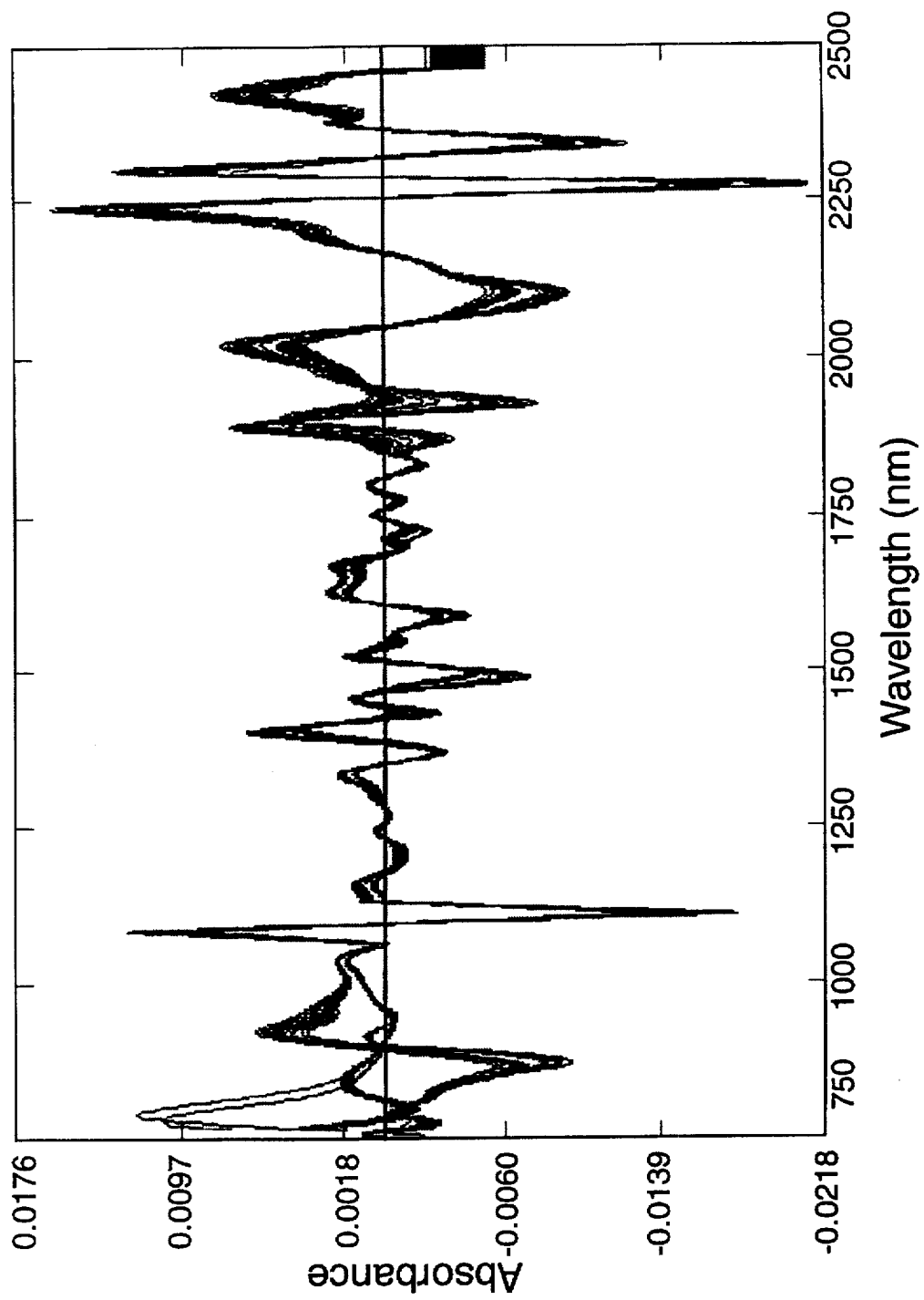
FIG. 3 is a plot of the second derivatives of the same data plotted in FIG. 1.

FIG. 3 shows the second derivatives of the same values as shown in FIG. 1 plotted as a family of tracings. Taking second derivatives further enhances the differences between plots of values from counterfeit and genuine bills.

Use of expanded scales also can make the distinctions between counterfeit and genuine currency even easier to observe. This can be seen in FIG. 4 which is an expanded scale plot of the values shown in FIG. 2 for the wavelengths from about 850 to about 950 nm.

Figure 5:
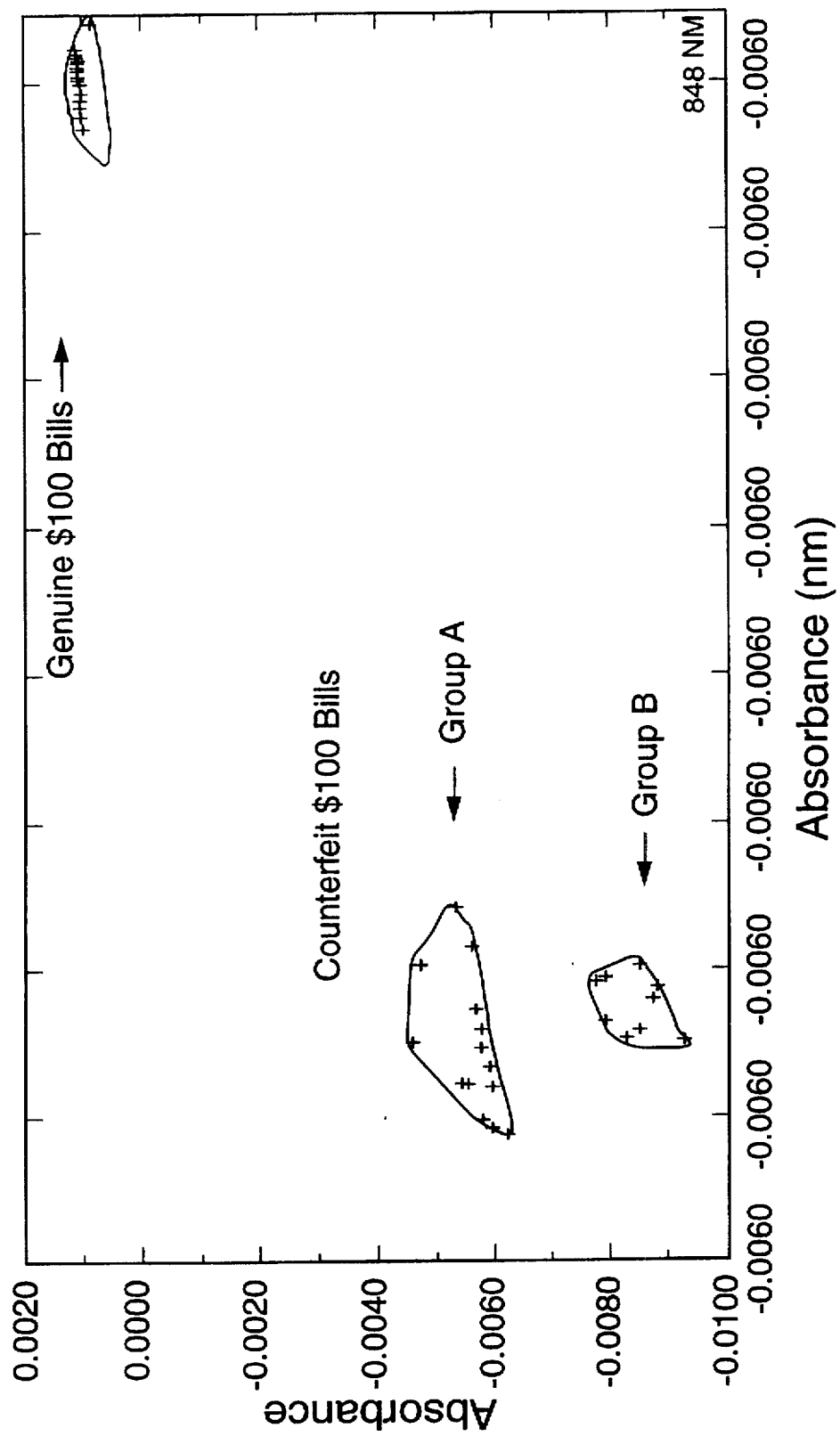
FIG. 5 is a two-dimensional cluster plot of the same data plotted in FIG. 1.
Figure 6:
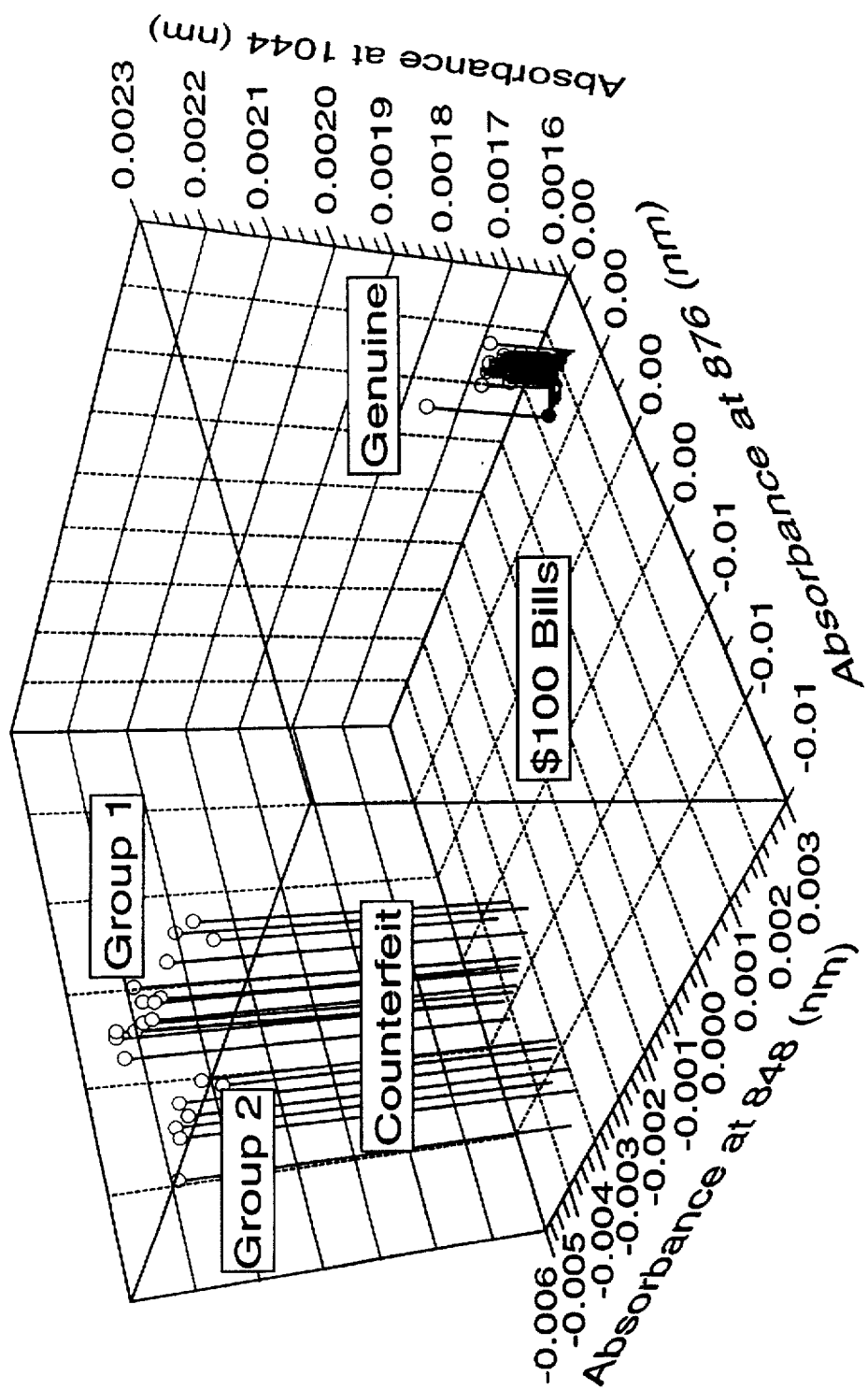
FIG. 6 is a three-dimensional cluster plot of the same data plotted in FIG. 1.

FIGS. 5 and 6 are examples of the same data plotted as clusters at two and three different wavelengths, respectively. FIG. 5 is a two-dimensional cluster plot. The two groups of data points in the lower left quadrant of the grid are attributable to counterfeit bills of two different types of ink used by the counterfeiters. The group of data points in the upper right quadrant of the grid are attributable to those generated from scans of genuine bills. From this figure it can be seen that reliable determinations easily can be made using two-dimensional cluster plots.

However, as can be seen from FIG. 6, use of a three-dimensional plot shows greater separation of the data points of genuine currency from the data points of counterfeit currency, and thus presumably more certainty in the determination of which samples are counterfeit.

Generally, the most useful wavelengths for the practice of this invention are those from about 750 nanometers to about 1250 nanometers because within that range are the wavelengths where there are the greatest differences between the reflectance data from genuine bills and the reflectance data from counterfeit bills. Presently preferred are wavelengths in the range between 800 and 1100. Presently most preferred are wavelengths in the range between 850 and 950. The most preferred wavelengths depend upon what instrumentation is being used, the denomination of the bills being tested and the type of manipulation and plotting of the data to be employed. Discontinuity in the patterns of wavelengths can be caused by changing detectors.

The spectral range from wavelengths of about 400 to about 750 nanometers does probably, as a practical matter, not provide much useful information in the detection of counterfeit bills in most circumstances because human optical ability would likely permit unaided observation to perceive differences in the bills which occurred within this range of wavelengths. These wavelengths could be used when there is to be no human observation of the bills.

If using the reflectance of the selected wavelengths does not clearly, unequivocally resolve the question of whether a bill is counterfeit, particularly if new types of counterfeit bills are put into circulation, a larger data base with additional factors (reflectance of other wavelengths caused by differences in paper, ink or fibers) can be used for detection.

Other factors such as moisture content and soiling with oils such as those from fingerprints can be analyzed using near infrared. Moisture content can be analyzed using wavelengths at approximately 1450 nanometers and about 1940 nanometers. Oils from human contact can be analyzed using wavelengths in the range from approximately 2100 nanometers to about 2300 nanometers.

The methods of this invention are nondestructive and can be nearly instantaneous. Use of near-infrared spectroscopy to scan bills requires very little setup.

Minimally required for a typical commercial application of the counterfeit currency detector are a power supply, a near-infrared light source, currency holder, wavelength selector, sensor, and a computer with a read-out device of some sort.

The wavelength selector can be as simple as a pair of interference filters. This would likely be less expensive and easier to incorporate than a single interference filter that must be tilted through a well-defined angle and whose position must be calibrated and correlated with the sensor's output. Other useful wavelength selectors include, but are not limited to gratings, prisms, acousto-optic tunable filters, and laser diodes.

For example, a handheld fiber optic probe can be placed in contact with a bill to be tested and a determination made in a matter of seconds as to whether the bill is counterfeit or genuine United States currency.

The sensor and wavelength selector needed for field use of the invention can be packaged into a small box. The accompanying computer can be a small lap-top model that is built into the box or is in a briefcase type of container and attached to the sensor and wavelength selector with a short cable as shown schematically in FIG. 7. The equipment can be battery-powered for field use or can be line-powered for use in a fixed location.

Figure 7:
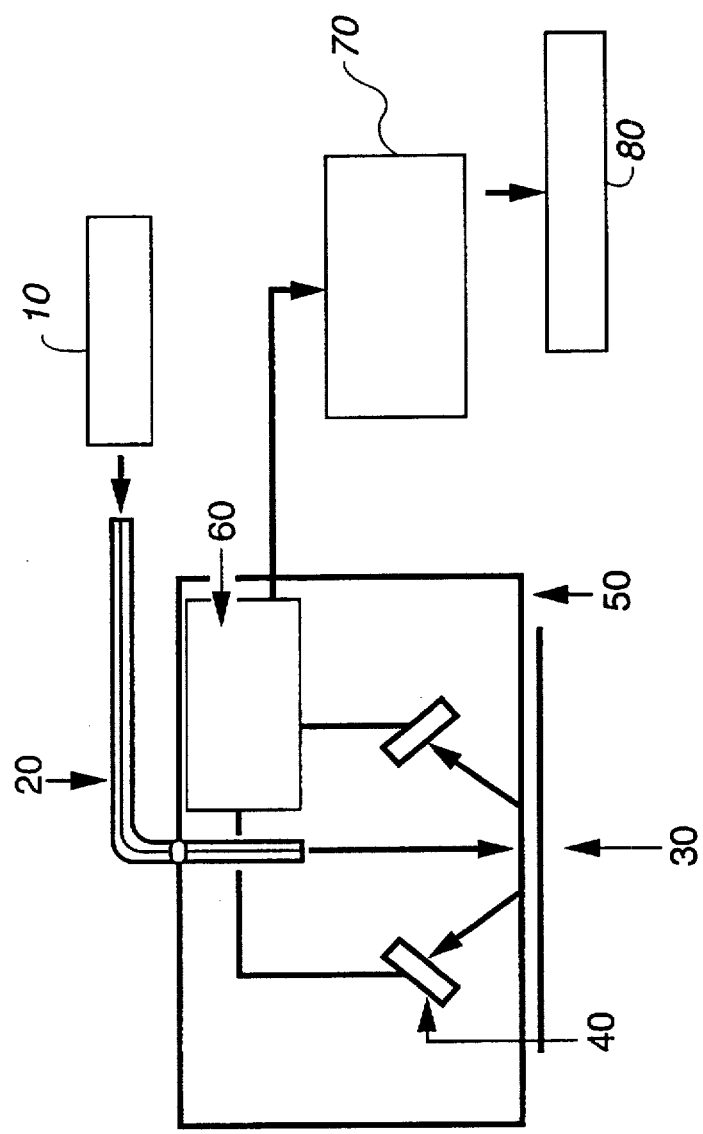
FIG. 7 is a schematic of an example set up of an apparatus for field use of the invention.

With reference to FIG. 7, a monochromator 10 is used to provide near infrared light which travels through a fiber optic cable 20 to a position from which it can be beamed onto the currency 30 to be tested. Sensors 40 in a remote reflectance probe 50 measure the intensity of reflected beams, digitize signals, and transmit signals through sensing electronics 60 to a temporary storage module in a spectrophotometer 70. The data is then transmitted to a computer 80 which compares the data from the current scans with data in the computer memory. A display on the computer 80, an LED, an auditory signal, or other indicating device can be used by the operator to observe the determination of whether the bills are counterfeit or not.

A combination of a fast-scan instrument, efficient bill-handling mechanism and computer with pre-loaded software can analyze several bills per second. The distinction between genuine and counterfeit currency can be made in a matter of milliseconds. The likelihood of error in determining whether a bill is genuine or counterfeit can be virtually eliminated by testing the library or database of reflectance patterns with a set of bills known to be genuine and a set of bills known to be counterfeit. If the discrimination between the sets is not sufficiently clear using the selected algorithm for processing the reflectance data, then the areas of the surface of the bills to be scanned, the wavelengths to be used, or the algorithm to be used can be changed.

Even if counterfeiters become sophisticated enough to make bills which mimic the patterns of near-infrared reflectance from genuine currency being used for comparison purposes, updating the detection equipment of this invention can be easily accomplished. The software being used could easily be changed by simply loading the computer being used with a library of patterns produced by reflectance from different specific areas on the bills and/or with different wavelengths. The new software would provide for comparison of different areas on the bills at different wavelengths, which would not be the ones the counterfeiters had been using to replicate the patterns previously used for comparison. Alternatively, loading a new library most likely would not be necessary, since use of a different algorithm for analyzing the data would show differences between the counterfeit bills and genuine currency that would not show up if the previous algorithm is foiled by counterfeiters. For example, if raw reflectance data is being compared, then a change to absorbance, or derivatives of reflectance or absorbance, or vectors could be made. A new threshold for discrimination could be selected.

The following examples will demonstrate the operability of the invention.

EXAMPLE I

A set of runs were made for the purpose of determining the ranges of wavelengths in which the differences between genuine and counterfeit currency would be greatest and thus most easily and reliably determined.

Thirty genuine US $100 bills from a local bank and 24 counterfeit US $100 bills which had been obtained from the Albuquerque Office of the Secret Service were used in the runs of this example. The genuine bills included 10 old bills, 10 new bills, and 10 bills in average circulated condition. The 24 counterfeit US $100 bills were "Supernotes".

Each of the counterfeit and genuine bills was scanned with a remote fiber optic reflectance probe attached to an NIR Systems™ Model 6500 spectrophotometer.

A 3"×3" mask was fabricated from a sheet of white Teflon™. A rectangular hole about 5 mm×15 mm was cut in the center of the Teflon™ sheet. The Teflon™ mask was centered over the 2"×2" quartz window of the reflectance probe and hinged on one side.

Each bill was positioned on a white Teflon background under the probe in the center of the quartz window, thereby placing the sample about 1" from the sensors inside the probe. The bill and mask combination was positioned so that an inked portion on the back side of each bill could be contacted by the near-infrared beams. The beam was perpendicular to the surface of the currency.

Wavelengths over the range from 400 nm to 2500 nm were scanned over the selected zone on each of the bills. Reflectances of infrared light from an angle of 45 degrees were measured by the probe.

The reflectance data from 750 mm to 2500 mm was analyzed.

The reflectance data from the probe was converted into absorbance data using NSAS software to perform the following conversion:

$$\text{Absorbance} = \text{Log}(1/\text{Reflectance})$$

A plot of the absorbance data showed that there were many positions in the spectra where differences between the plots of the scans of the genuine bills and the counterfeit bills were sufficient to perform discriminant analysis. Discriminant analysis was performed in the region from 750 nm to 2500 nm. This plot is shown in FIG. 1.

With reference to FIG. 1, the more flat family of tracings which is uppermost at about 900 nm represent the data generated from scans of the bills known to be genuine. The family of tracings which loops lowest in the plot and which has the bifurcation of lower loops forming two sub-groups A and B are tracings of the absorbance data from the group of counterfeit bills. The fact that the tracings fell into two separate sub-groups was attributed to the use of two different ink recipes used by the counterfeiters in making the counterfeit bills.

A plot of first derivatives of the absorbances (y coordinate) associated with the wavelengths (x coordinate) for each of the scans was made and is shown in FIG. 2.

Then second derivatives were taken of the data points of absorbance as a function of wavelength of the original spectra. The second derivatives of the data points of the spectra were then subjected to a discriminant analysis program to identify the wavelengths which showed the most difference between genuine and counterfeit bills. A plot of the second derivatives of the data points of the spectra of each of the scans of the genuine and of the counterfeit bills is shown in FIG. 3.

Figure 4:
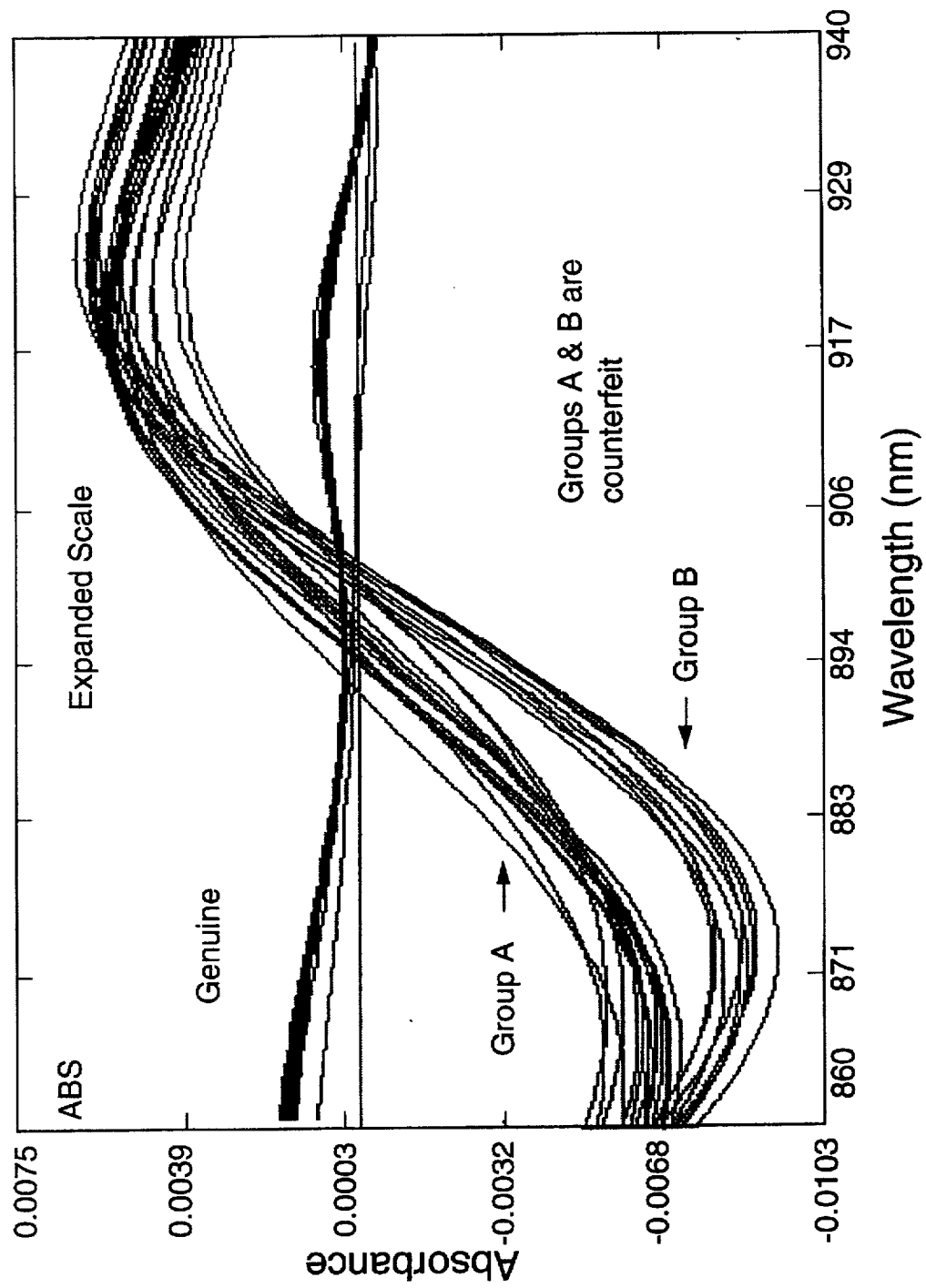
FIG. 4 shows a portion of the data of FIG. 2 from wavelengths from about 850 nm to about 950 nm plotted on an expanded scale.

The area from wavelengths of about 875 to about 925 is expanded and shown in FIG. 4. The group of generally flat tracings is the plot of the 30 genuine notes. The generally curved tracings are a plot of the absorbance data from scans of the counterfeit notes.

The first derivatives of the data points of the spectra at wavelengths of 848, and 876 were plotted on a two-dimensional grid, as shown in FIG. 5. FIG. 5 shows separations of the groups of data points in two dimensions. Each elliptically shaped cluster has a "center of mass" and an associated standard deviation that is direction-dependent. The distance from one cluster to another is measured in Mahalanobis units.

A Mahalanobis unit is the distance from the center of a cluster to the edge of the ellipse that defines that cluster, in the direction of the point representing a test sample. Because the Mahalanobis unit is direction dependent, it is non-Euclidian and changes for various directions. If the ellipse represents one standard deviation of the members of that group (which is typical), then a point within about 3 Mahalanobis units is very likely to be a member of that group. Distances of greater than 7 Mahalanobis units indicate that the chances of the data point belonging to that group are extremely small. Distances of 20 Mahalanobis units are virtually certain to indicate that the data point at that distance is not a member of the group.

FIG. 6 is a three-dimensional representation of the same data shown in the two-dimensional discriminant plot of FIG. 5. The data points representing the group of genuine bills are tightly packed in the lower right front corner of the box, and the data points representing the supernotes are the nine points nearest the upper left corner, near the back wall.

In the results from the runs of this example, the separation of the group of genuine bills from the group of counterfeit bills in the three-dimensional plotted space was greater than 25 Mahalanobis units. As noted above, any Mahalanobis value over 7 is considered significant for discrimination between the groups of data points representing the samples.

The separation of the two counterfeit groups exceeds 13 Mahalanobis units. Both numbers are measurements in 3 dimensions; this difference is less apparent in two-dimensional plots.

This example demonstrated that at wavelengths from about 850 nm to about 900 nm, from about 1000 nm to about 1050 nm, and from 1050 nm to about 1100 nm there were significant differences between plots of data from genuine bills and plots of data from counterfeit bills. These differences could be used to readily determine whether a bill which was not one of the ones used to obtain the data in this example is counterfeit or not simply by scanning the bill to be tested in the manner the bills used in this example were scanned.

EXAMPLE II

A set of runs was made to demonstrate operability of the invention with scans of un-inked portions of US $20 bills. An NIR System™ Model 6500 spectrophotometer with a remote fiber optic reflectance probe was used to analyze seven genuine US $20 bills from a local bank and ten counterfeit US $20 bills which had been obtained from the Albuquerque, N. Mex., Office of the Secret Service.

A first set having 7 genuine bills and 10 counterfeit bills was used as a training set to build a database or library in the computer.

A 3"×3" mask was fabricated from a sheet of white Teflon™. A rectangular hole about 5 mm×15 mm was cut in the center of the Teflon™ sheet. The Teflon™ mask was centered over the 2"×2" quartz window of the reflectance probe and hinged on one side.

13

Each bill was positioned on a white Teflon background under the probe in the center of the quartz window, thereby placing the sample about 1" from the sensors inside the probe. The bill and mask combination was positioned so that a portion of the bill having only paper without ink could be contacted by the near-infrared beams. The beam was perpendicular to the surface of the currency.

Three zones were selected on the front side of each genuine and counterfeit bill (far left, left of center, and far right). The selected zones were un-inked portions of the bills, thusly providing reflectance of near infrared light from paper only. Using the same three zones on each of the bills provided a total of 51 spectra: 21 spectra for genuine bills and 30 spectra for counterfeit bills. Fifteen scans were made of each of the zones on each of the bills.

Wavelengths over the range from 400 nm to 2500 nm were scanned over each of the selected zones on each of the bills. Reflectances of infrared light from an angle of 45 degrees were measured by the probe.

The reflectance data from 750 mm to 2500 mm was analyzed.

The reflectance data from the probe was converted into absorbance data using NSAS software to perform the following conversion:

Absorbance=Log(1/Reflectance)

Figure 8:
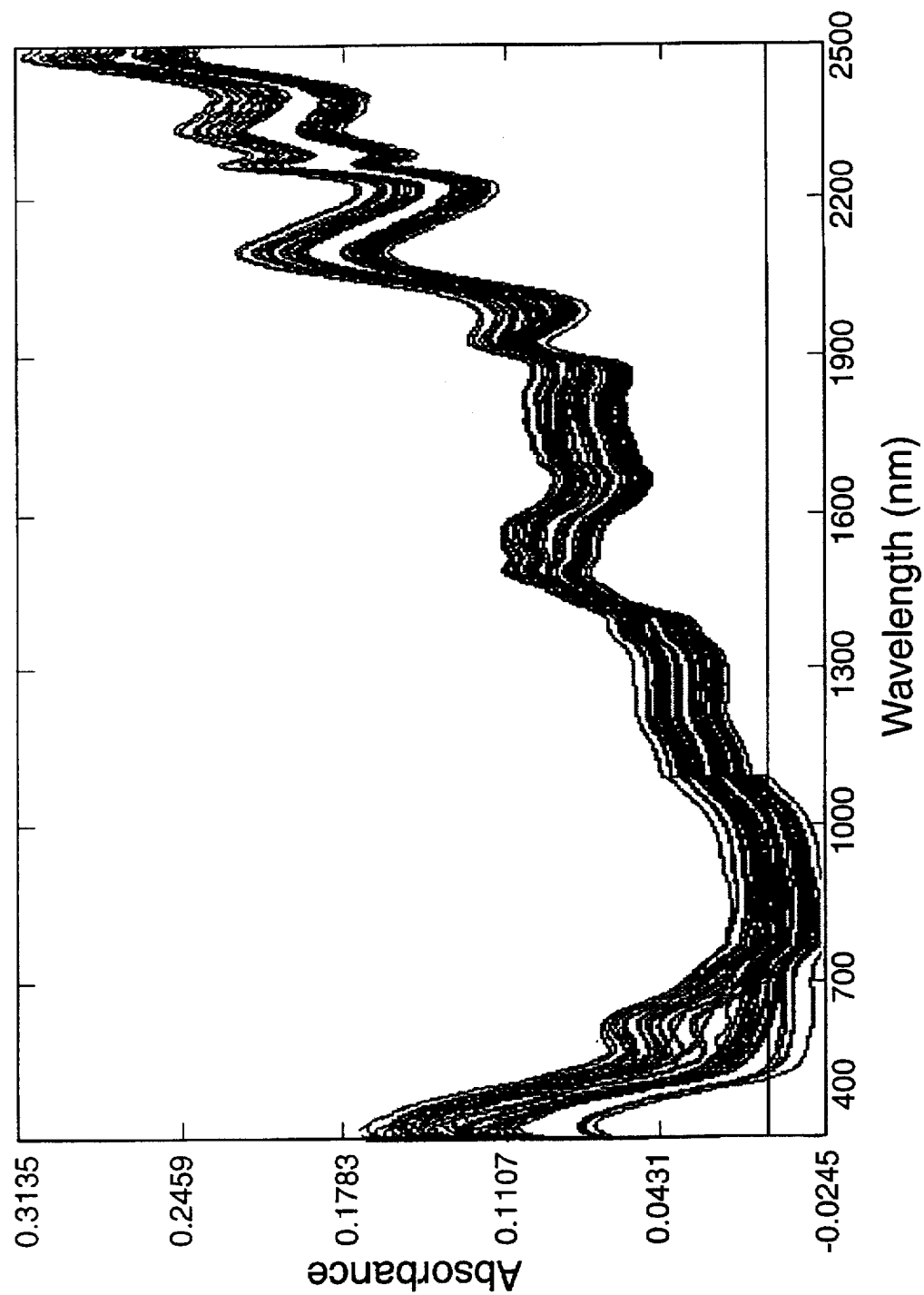
FIG. 8 is a plot of the absorbances as a function of wavelengths for scans made of un-inked portions of groups of genuine and counterfeit $20 bills.

A plot was made of the absorbance as a function of wavelength data and is shown as FIG. 8.

Figure 9:
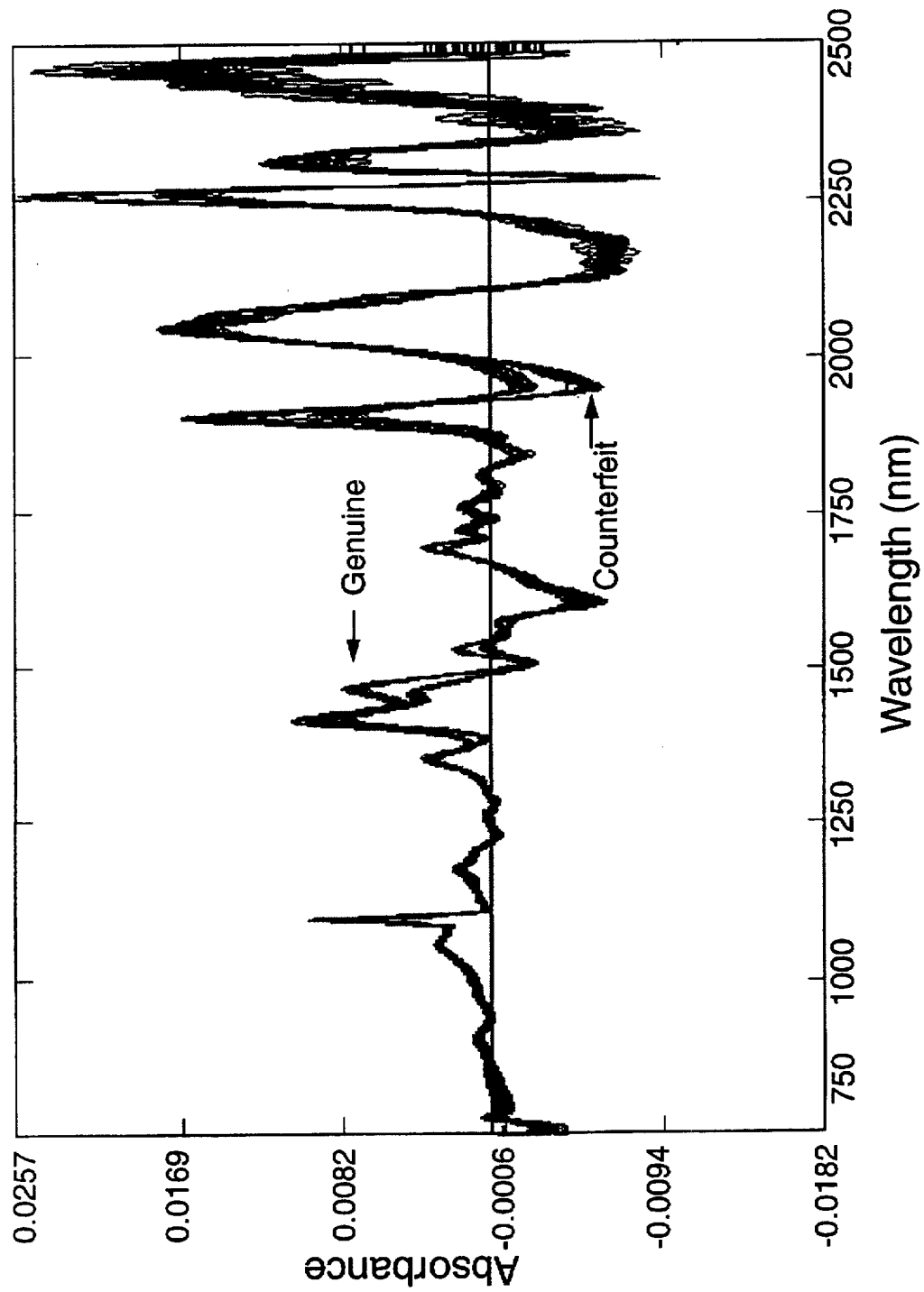
FIG. 9 is a plot of the first derivatives of the data plotted in FIG. 8.

A plot of first derivatives of the absorbances (y coordinate) associated with the wavelengths (x coordinate) for each of the scans was made and is shown in FIG. 9.

There were many positions in the spectra where differences between the plots of the scans of the genuine bills and the counterfeit bills were sufficient to perform discriminant analysis. Discriminant analysis was performed in the region from 750 nm to 2500 nm.

Figure 10:
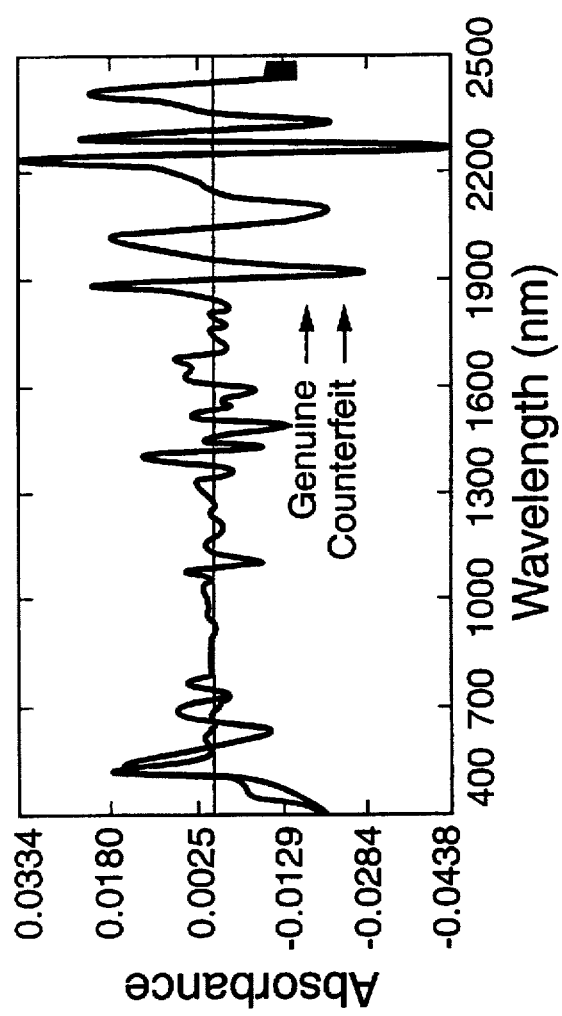
FIG. 10 is a plot of the second derivatives of the data points of the spectra plotted in FIG. 8.

Then second derivatives were taken of the data points of absorbance as a function of wavelength data points of the original spectra. A plot of the second derivatives of the data points of the spectra of each of the scans of the genuine and of the counterfeit bills is shown in FIG. 10.

The second derivatives of the data points of the spectra were then subjected to a discriminant analysis program to identify the wavelengths which showed the most difference between genuine and counterfeit bills.

Figure 11:
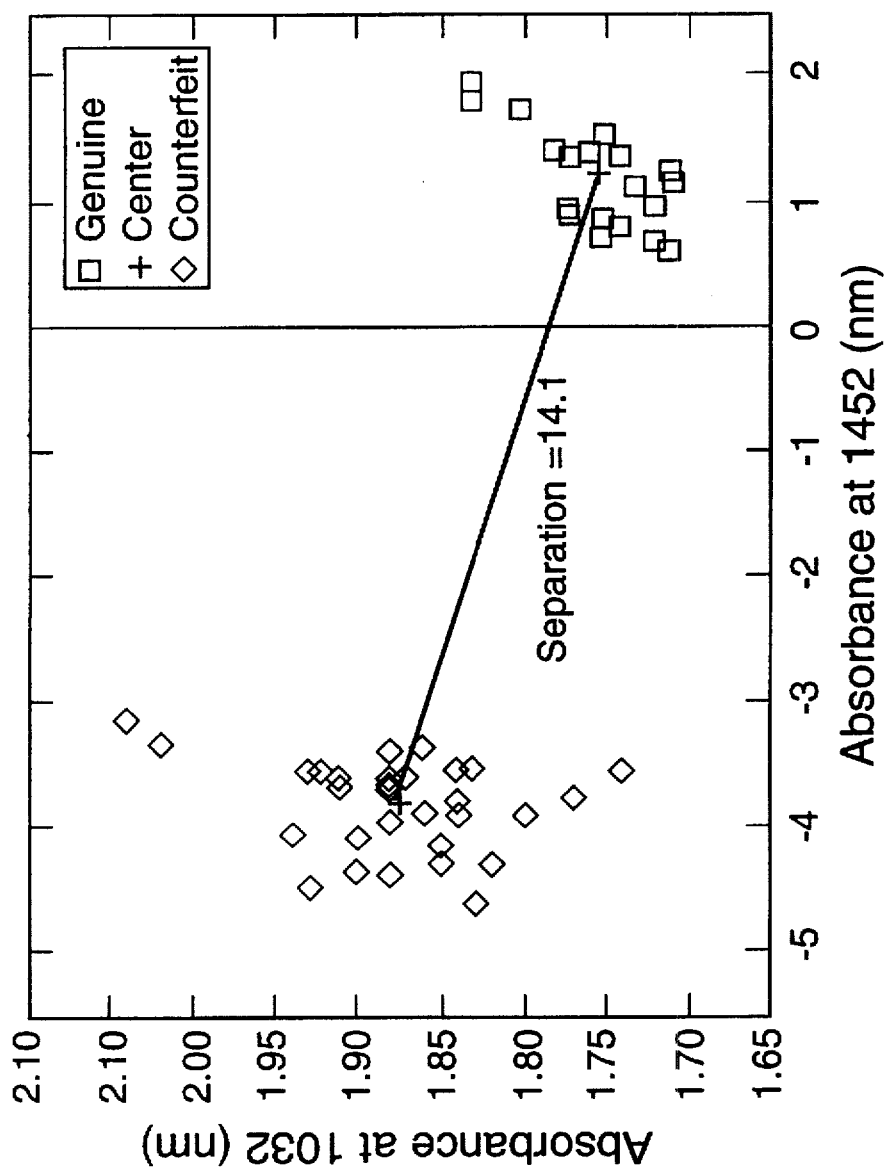
FIG. 11 shows a two-dimensional cluster representation of the data depicted in FIG. 8.

The first derivatives of the data points of the spectra at wavelengths of 1452 nm and 1032 nm were plotted on a two-dimensional grid, as shown in FIG. 11. The data points representing the absorbances of the genuine and counterfeit bills are clearly separated into two different clusters; the cluster in the lower right portion of the grid are the data points associated with the genuine bills.

The separation of the group of genuine bills from the group of counterfeit bills in the two-dimensional plotted space was 14.1 Mahalanobis units. Any Mahalanobis value over 7 is considered significant for discrimination between the groups of data points representing the samples.

This example demonstrated that at wavelengths around 1452 nm and 1032 nm there were significant differences between plots of data from genuine bills and plots of data from counterfeit bills. These differences could be used to readily determine whether a bill which was not one of the ones used to obtain the data in this example is counterfeit or not simply by scanning the bill to be tested in the manner the bills used in this example were scanned.

14

EXAMPLE III

A set of runs were made using 60 genuine US $100 bills and 24 counterfeit US $100 bills to demonstrate use of a Lotus 1-2-3 spreadsheet to display differences in the spectra from the respective groups of bills. This is the same set of bills described in Example I plus an additional 30 genuine bills.

The counterfeit bills were "Supernotes" obtained from the United States Secret Service. The initial 30 genuine bills included 10 old, very worn bills, 10 new bills, and 10 bills in average, circulated condition. The additional 30 genuine bills were currency issued in the 1960's, 1970's and 1980's obtained from Los Alamos National Bank.

The bills were scanned in the same manner described in Example I using an NIR System™ Model 6500 spectrophotometer with a remote fiber optic reflectance probe. The bills were sandwiched between the Teflon™ mask and block described in Example I so that only an area on the back of each of the bills in the center of the "tower" portion of the photograph was scanned. Scanning this portion of each of the bills resulted in scans of paper and ink.

Scanning was done over the entire near infrared range (750–2500 nm) in 2 nanometer increments.

The Model 6500 monochromator performed the conversion of the reflectance data into electrical signals which were then fed to an IBM 386 PC.

The IBM 386 PC had been loaded with NIR Systems' "NSAS with IQ$^2$" software which directed the Model 6500 spectrophotometer to: (1) scan over the selected range of 400 to 2500 nm; (2) temporarily store the resulting wavelength/absorbance pairs in the memory of the spectrophotometer; and (3) send this data to memory it had reserved in the accompanying computer.

Discriminant analysis of the absorbance vs. wavelength data from the scans of each of the bills was also made using "IDAS with DISCRM" software from Bran+Luebbe to identify the wavelengths necessary and sufficient to correlate the corresponding absorbances (or derivatives thereof) with concentrations (in the case of quantitative analysis) or with spectral patterns (in the case of qualitative analysis, such as that used to classify the counterfeit currency in this example).

The reflectance data from 750 nm to 2500 nm was analyzed. The reflectance data from the probe was converted into absorbance data using the NSAS software to perform the following conversion:

Absorbance=Log(1/Reflectance)

Figure 12:
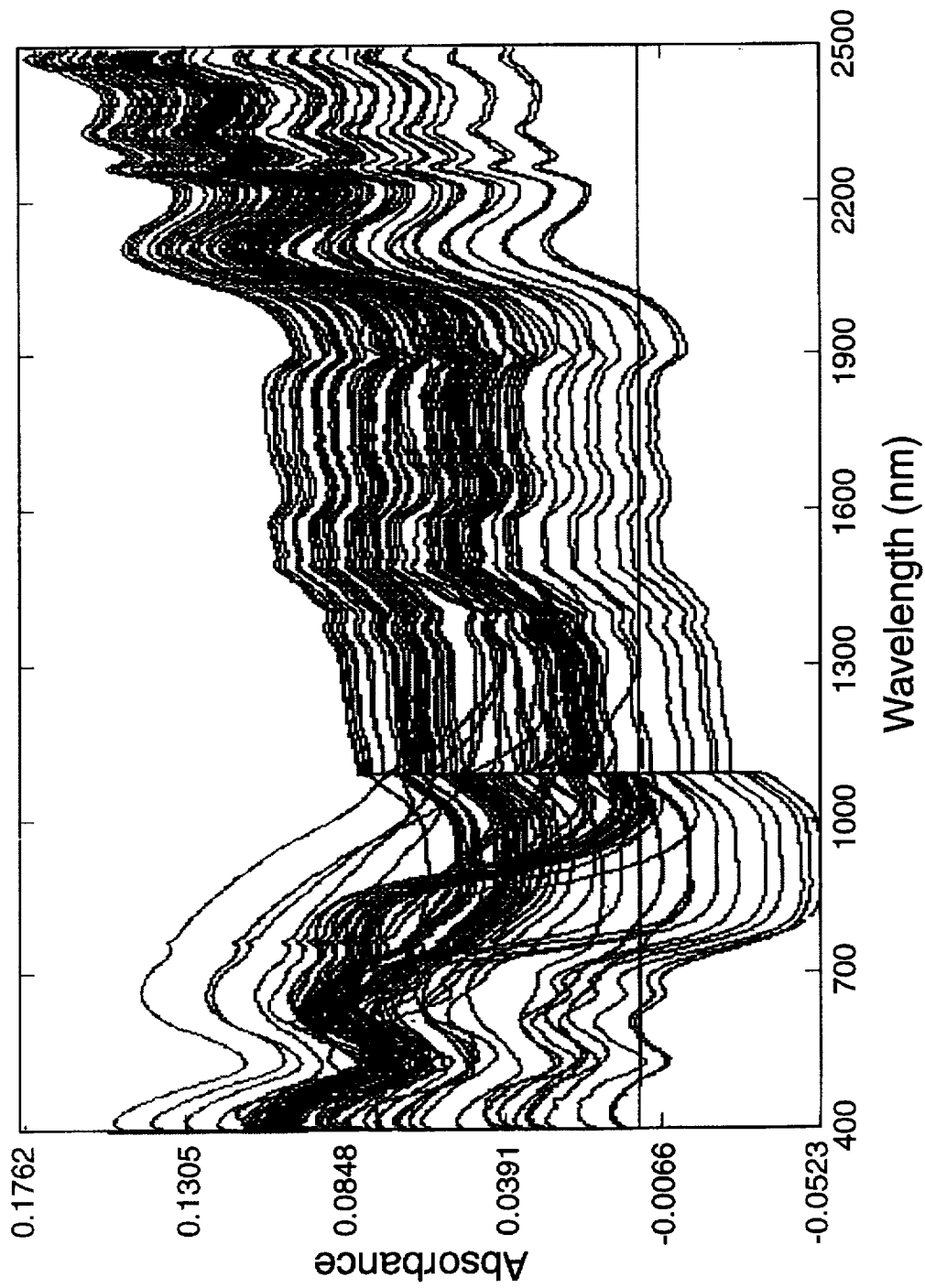
FIG. 12 is a plot of the absorbances associated with the wavelengths for scans made of 84 genuine and counterfeit $100 bills.

A plot of the absorbance data as a function of the wavelength showed that there were many positions in the spectra where differences between the plots of the scans of the genuine bills and the counterfeit bills were sufficient to perform discriminant analysis, just as was shown in Example I. Again, discriminant analysis was performed in the region from 750 nm to 2500 nm. This plot is shown in FIG. 12.

Figure 13:
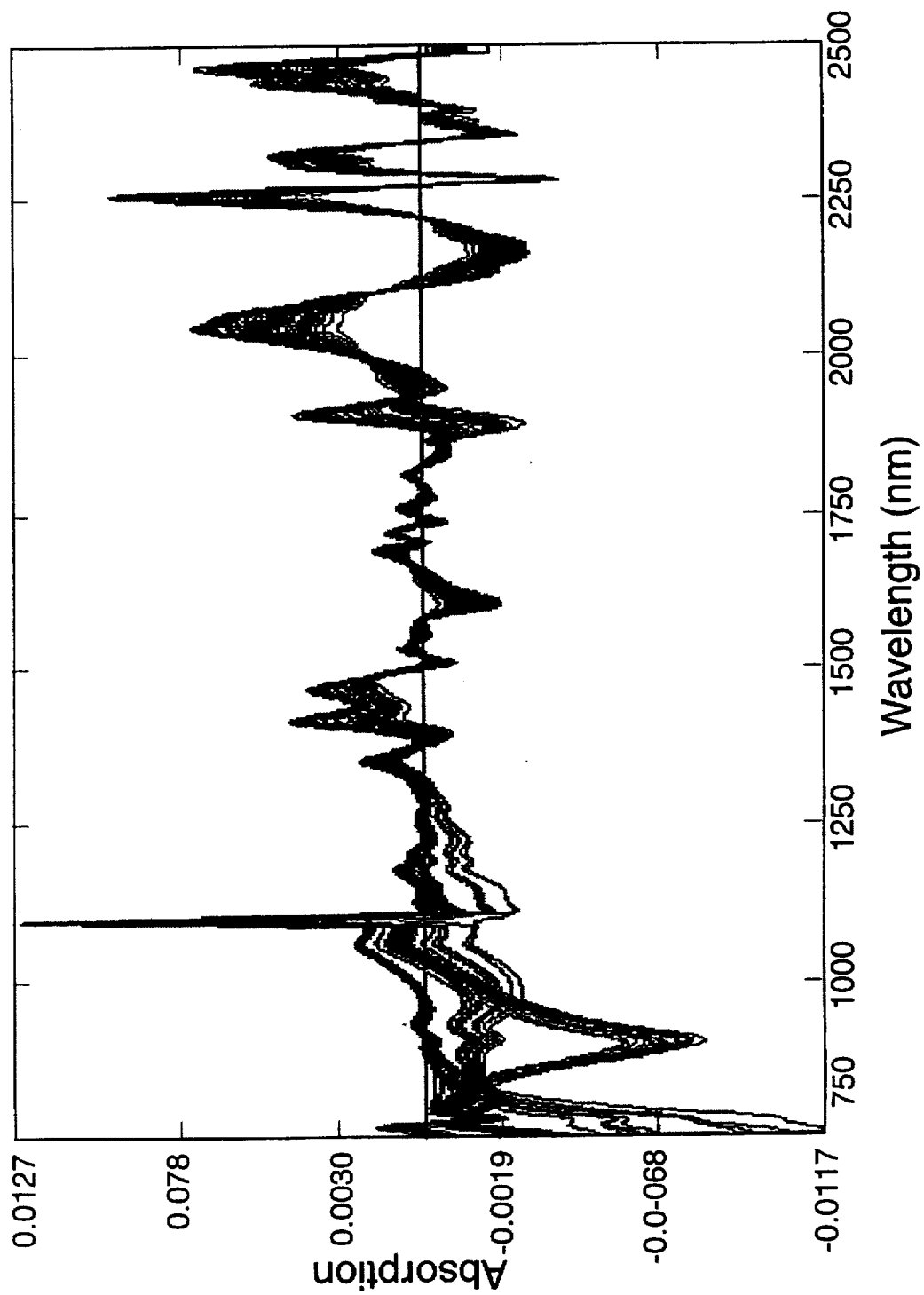
FIG. 13 is a plot of the first derivatives of the data plotted in FIG. 12.
Figure 14:
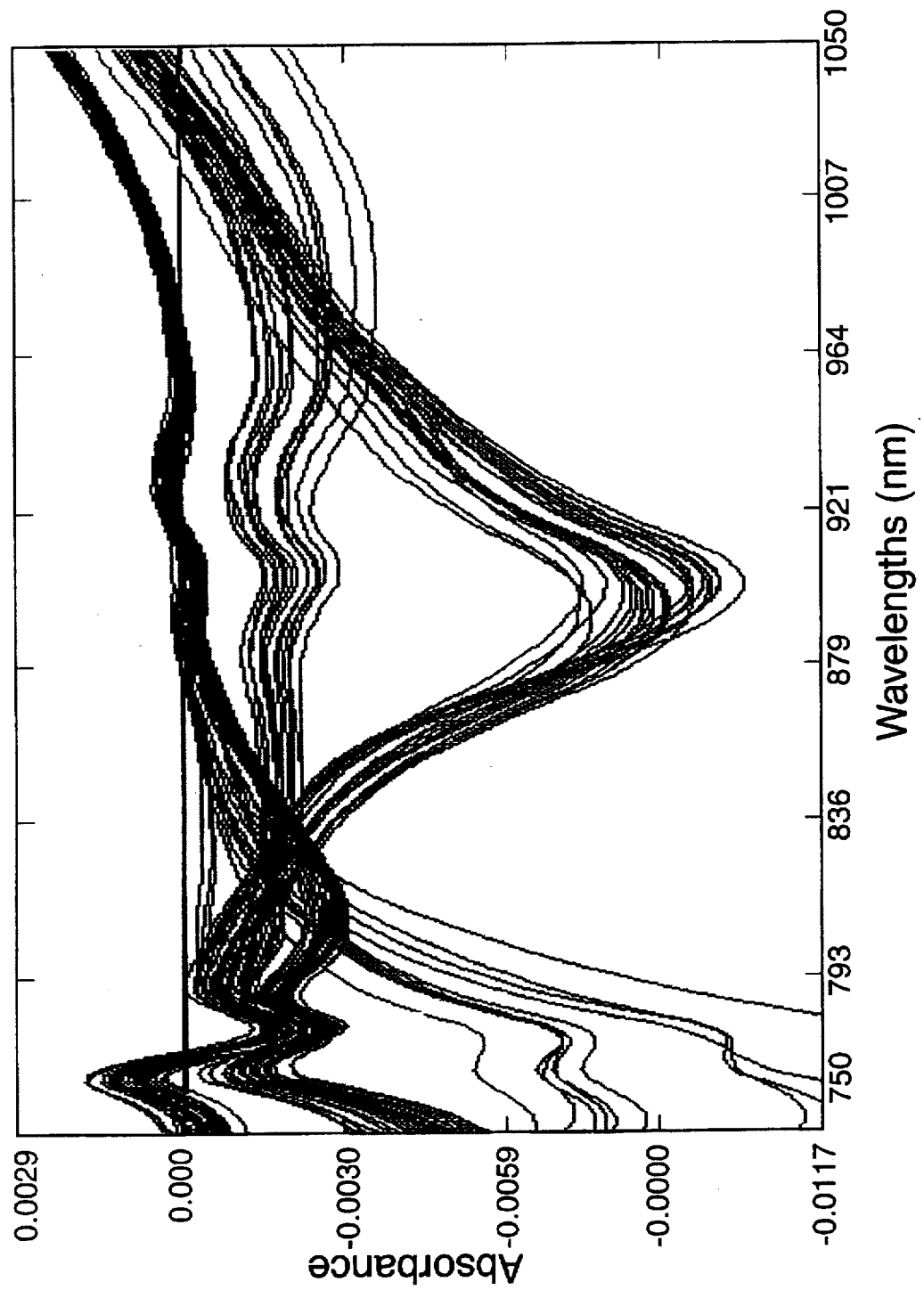
FIG. 14 is an expanded portion of the plot of the first derivatives of the data points of the spectra plotted in FIG. 13.

It can be seen from this plot that the largest differences between data from genuine currency and counterfeit currency occurred in the region between the wavelengths from about 836 nm to about 964 nm. This difference was seen even more clearly when the first derivative of the data were taken, as shown in FIG. 13. The area from wavelengths of about 750 nm to about 1050 nm was expanded, as shown in FIG. 14. Again, the differences between the data from genuine and counterfeit currency were further emphasized.

Figure 15:
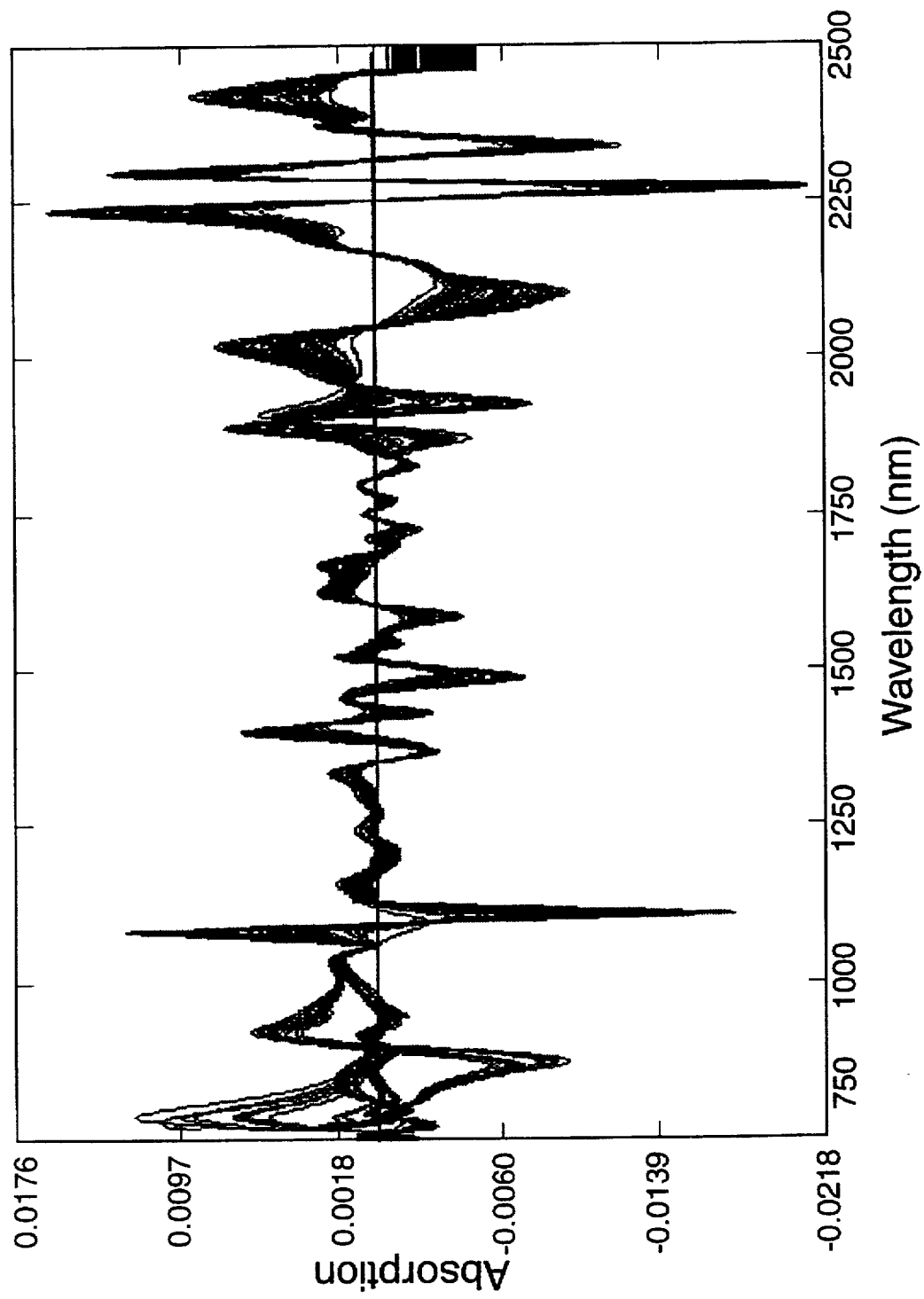
FIG. 15 shows a family of tracings of the second derivatives of the same data as plotted in FIG. 2.
Figure 16:
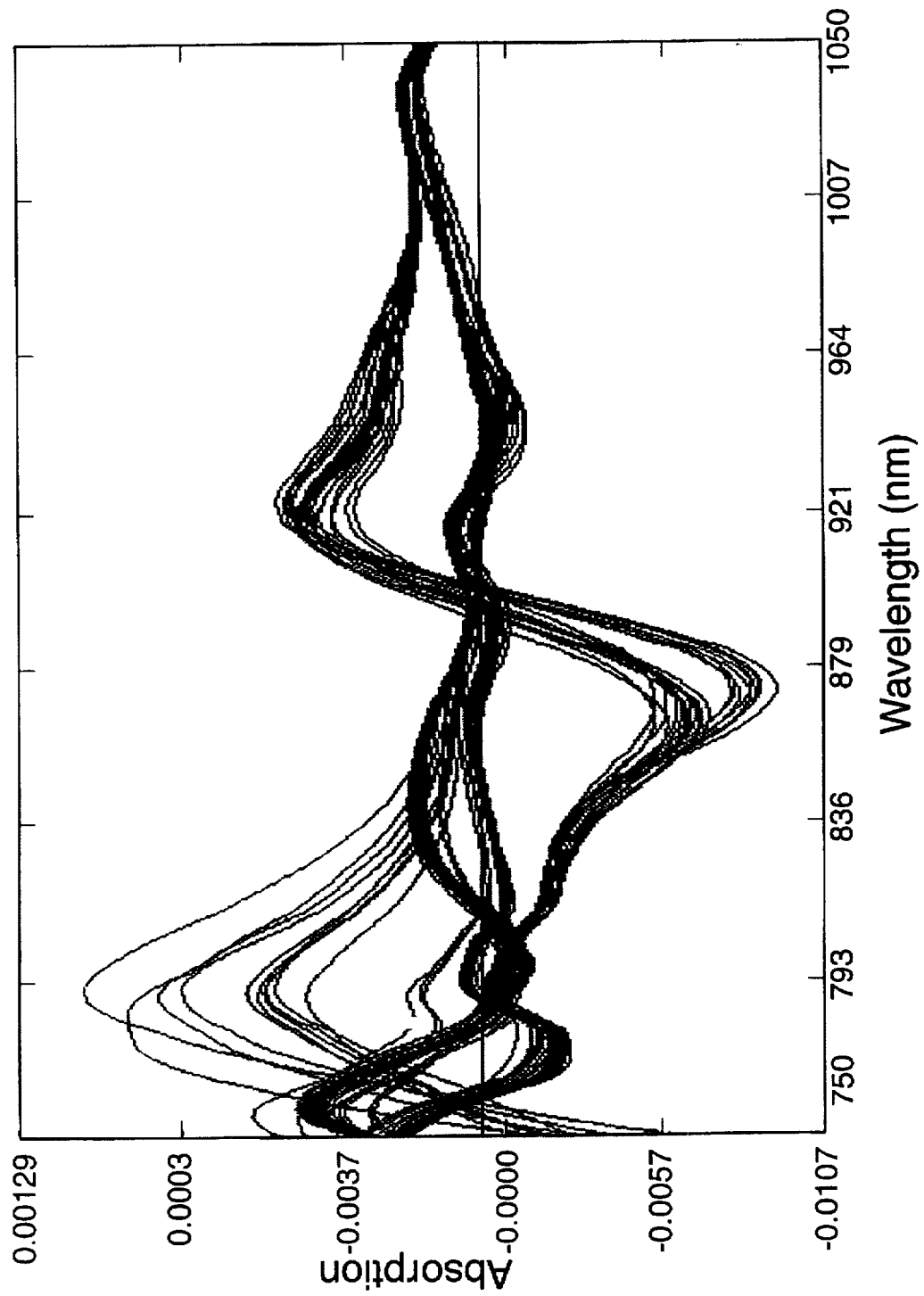
FIG. 16 shows an expanded portion of the plot of the second derivatives plotted in FIG. 15.

Second derivatives were taken of the same data and plotted as shown in FIG. 15. The wavelengths from 750 nm to 1050 nm are shown on an expanded scale in FIG. 16.

Figure 17:
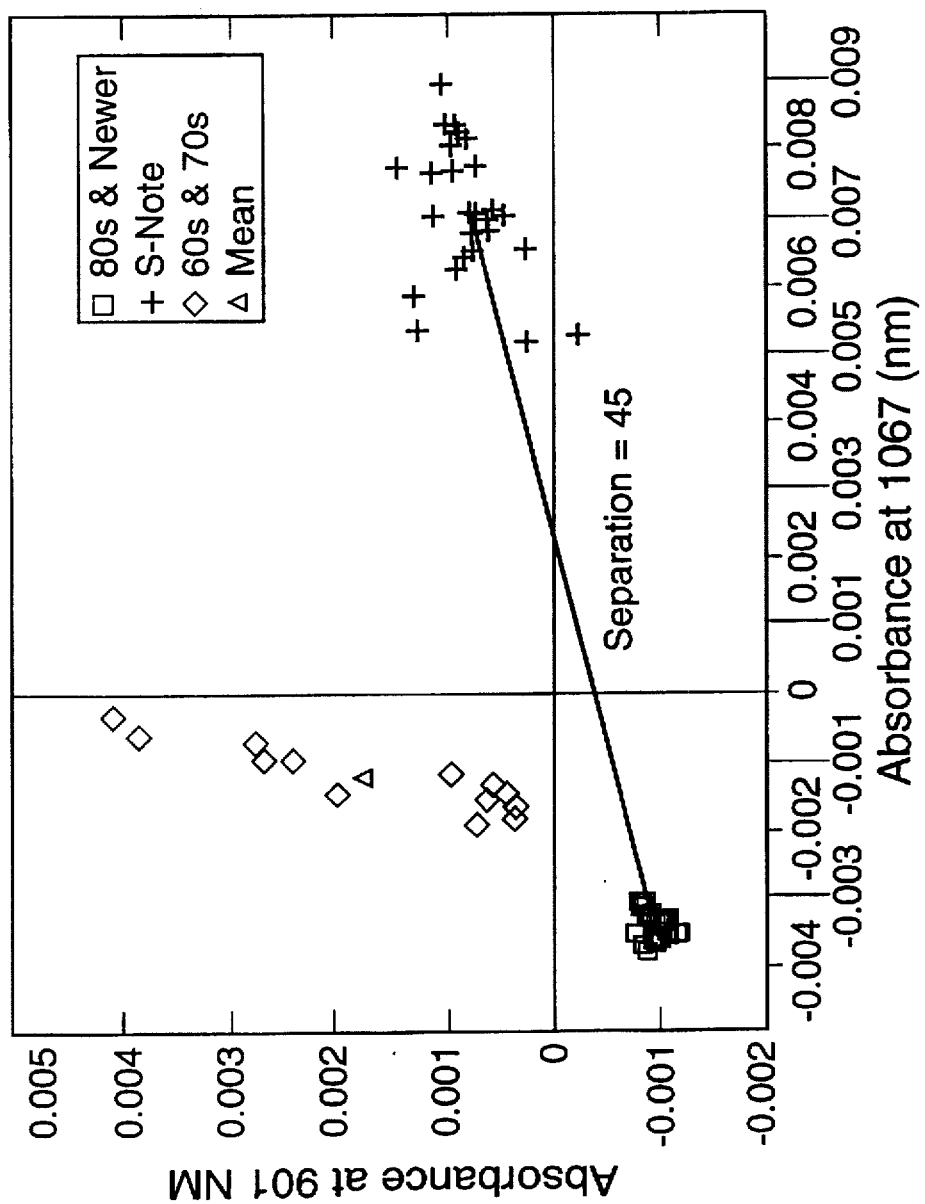
FIG. 17 shows a two-dimensional cluster representation of the data depicted in FIG. 12.

The absorbance values from the files produced by the NSAS software were also entered into Lotus 1-2-3 spreadsheet software and plotted for each of two wavelengths on a two-dimensional cluster plot. The plot is shown as FIG. 17. The +'s represent the individual data points of the "supernote" counterfeit bills. The diamonds represent data points of the genuine bills which were printed during the 1960's and 1970's. The squares represent data points of genuine bills printed in the 1980's.

Figure 18:
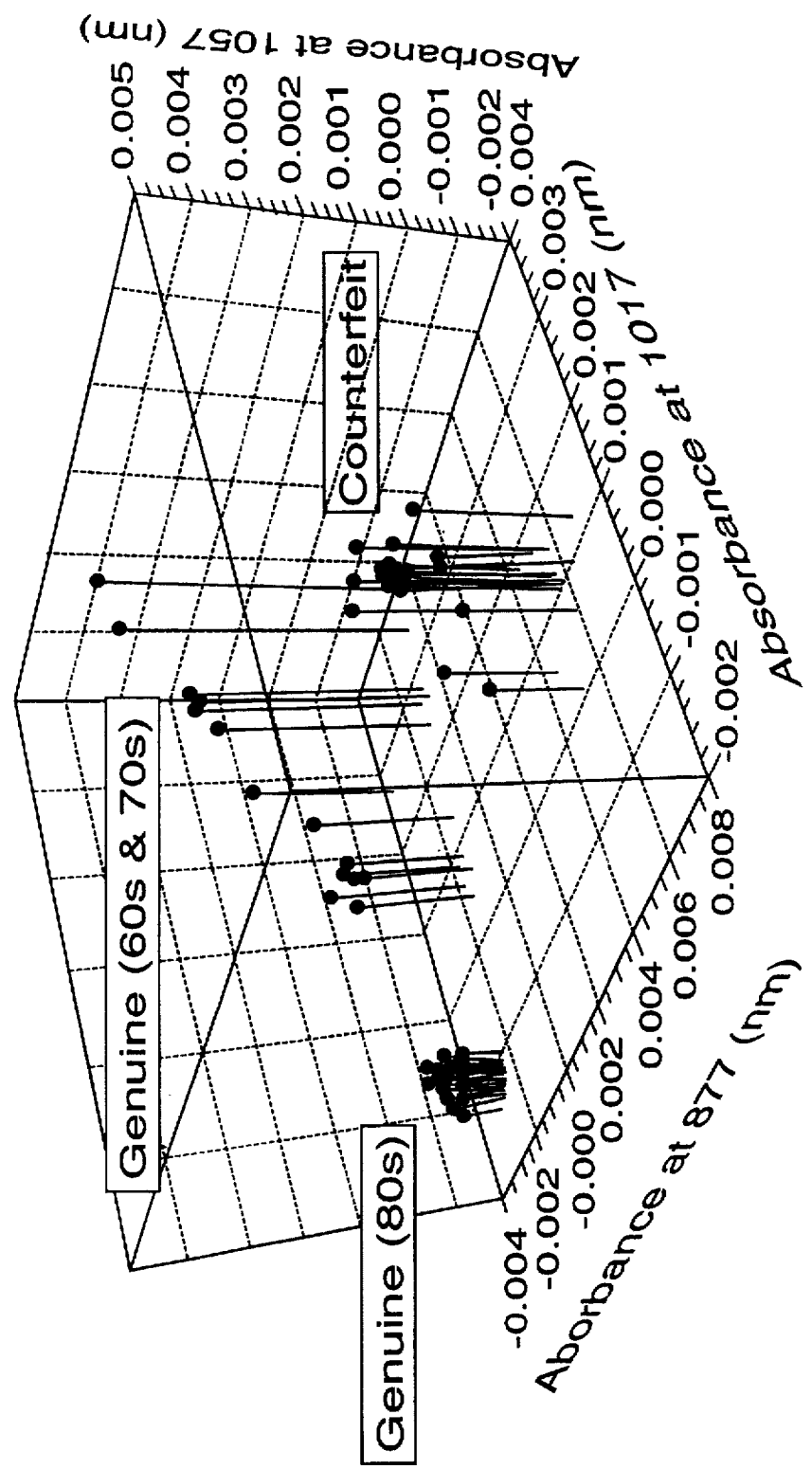
FIG. 18 shows a three-dimensional cluster representation of the data depicted in FIG. 12.

The differences between genuine and counterfeit currency can readily be seen by the distinct, clearly spaced groupings of the data points of each of the different bills scanned, with the data points grouped exactly in accordance with each of the three types of bills scanned. FIG. 18 is a three-dimensional plot of the same absorbance values at wavelengths of 877 nm, 1017 nm, and 1057 nm.

The counterfeit bills can readily be detected from the plots.

The use of the Lotus 1-2-3 spreadsheet software also demonstrates another of the multiple ways in which the data can be analyzed.

While the apparatuses and methods of this invention have been described in detail for the purpose of illustration, the inventive apparatuses and methods are not to be construed as limited thereby. This patent is intended to cover all changes and modifications within the spirit and scope thereof.

INDUSTRIAL APPLICABILITY

Banking industries and governments all over the world would find dependable methods and apparatuses such as those of the present invention valuable for insuring that the currency they deal with is genuine. Retail and entertainment establishments which handle high volumes of currency in the private sector would benefit greatly from having a simple, on-site, easily used method and apparatus for detecting counterfeit currency. Examples include gambling casinos, amusement parks, public transportation systems,

What is claimed is:

1. A method of detecting counterfeit currency comprising:

(a) contacting at least one selected area of currency known to be genuine with a near-infrared beam having at least two wavelengths in the electromagnetic spectrum below 1250 nanometers;

(b) measuring the intensity of the reflected portion of the portion of said near-infrared beam within said at least two wavelengths in the electromagnetic spectrum below 1250 nanometers reflected from said at least one selected area of said currency known to be genuine;

(c) contacting currency known to be counterfeit with a near-infrared beam having at least two wavelengths in the electromagnetic spectrum below 1250 nanometers reflected from said at least one selected area of said currency known to be counterfeit;

(d) measuring the intensity of the reflected portion of the portion of said near-infrared beam within said at least two wavelengths reflected from said at least one selected area of said currency known to be counterfeit;

(e) plotting the results of steps (b) and (d) to obtain two plots;

(f) comparing said two plots obtained from plotting the results of steps (b) and (d);

(g) selecting at least one wavelength at which said two plots of the results of steps (b) and (d) are most divergent;

(h) contacting currency to be tested with a near-infrared beam having at least one wavelength in the electromagnetic spectrum substantially identical to said at least one wavelength at which said two plots are most divergent;

(i) measuring the intensity of the reflected portion of said near-infrared beam within said at least one wavelength at which said two plots are most divergent which is reflected from said currency to be tested;

(j) comparing said intensity of said reflected portion of said portion of said near-infrared beam reflected from said currency to be tested with said plot obtained from step (b) to determine extent of divergence of portion of said near-infrared beam reflected from said currency to be tested from portion of said near-infrared beam reflected from said currency known to be genuine; thereby enabling a determination of whether said currency to be tested is genuine.

2. A method as recited in claim 1 wherein said currency known to be genuine is contacted with said near-infrared beam having wavelengths in all spectra from about 750 nanometers to about 1250 nanometers; and wherein said currency to be tested is contacted with said near-infrared beam having wavelengths in all spectra from about 750 nanometers to about 1250 nanometers.

* * * * *